United States Patent [19]
Zanette et al.

[11] Patent Number: 5,981,716
[45] Date of Patent: Nov. 9, 1999

[54] PROCESS FOR THE PURIFICATION OF PROTEINS

[75] Inventors: Dino Zanette, Pianzano; Edoardo Giacomo Sarubbi, Milan; Adolfo Soffientini, Sesto San Giovanni; Ermenegildo Restelli, Gerenzano; Armando Grigoletto, Mortara, all of Italy

[73] Assignee: Gruppo Lepettit, S.P.A., Gerenzano (Varese), Italy

[21] Appl. No.: 08/898,014

[22] Filed: Jul. 22, 1997

Related U.S. Application Data

[63] Continuation of application No. 08/475,260, Jun. 7, 1995, abandoned.

[51] Int. Cl.⁶ .......................... C07K 1/14; C07K 14/505
[52] U.S. Cl. ..................... 530/395; 530/412; 530/413; 530/414; 530/416; 530/417
[58] Field of Search .................... 530/395, 412, 530/413, 414, 416, 417

[56] References Cited

U.S. PATENT DOCUMENTS

| | | | |
|---|---|---|---|
| 4,568,488 | 2/1986 | Lee Huang | 260/112 |
| 4,667,016 | 5/1987 | Lai et al. | 530/397 |
| 5,300,490 | 4/1994 | Kunichiro et al. | 514/8 |
| 5,362,855 | 11/1994 | Garlick et al. | 530/385 |
| 5,478,754 | 12/1995 | Brandt et al. | 436/518 |

FOREIGN PATENT DOCUMENTS

| | | |
|---|---|---|
| 0358463 | 3/1990 | European Pat. Off. . |
| 2024829 | 1/1980 | United Kingdom . |
| 8604068 | 7/1986 | WIPO . |

OTHER PUBLICATIONS

Desnoyers et al.; Interaction of a Novel Class of Phospholipid–Binding Proteins of Bovine Seminal Fluid with Different Affinity Matrices; Arch. Biochem. Biophys., 1993, 305/2 341–349 (Abstract).

Williams et al.; Fractionation of Membrane Proteins on Phenylboronic Acid–Agarose; Biochem. J., 1982, 205, 167–171.

Gaudreault et al., Glycoprotein Nature of Glycosidases from Leaves of *Pisum sativum*L.; J. Exp. Botany, 34/146, 1145–1154.

De Cristofaro et al.; Human Platelet Glycocalicin Purification by Phenyl Boronate Affinity Chromatography Coupled to Anion–Exchange High–Performance Liquid Chromatography; J. Chromatography, 426, 1988, 376–380.

Ducrocq et al., 'Separation of Nonenzymatically Glycosylated Proteins by Phenylboronate Affinity Chromatography', Protides Biol. Fluids vol. 33, pp. 651–654, 1985.

File Caplus on STN No. 1991:551765. Wasley et al. 'The Importance of N– and O–Linked Oligosaccharides Fro the Biosynthesis and in Vitro and in Vivo Biologic Activities of Erythropoietin', Blood, vol. 77, No. 12, pp. 2624–32. (abstract only) 1991.

*Primary Examiner*—Michael P. Woodward
*Assistant Examiner*—Anish Gupta
*Attorney, Agent, or Firm*—Tracey B. Davies; Vinson & Elkins, L.L.P.

[57] ABSTRACT

The present invention is directed to a simple and efficient process for the recovery of a biologically active glycoprotein from a biological fluid containing it.

In a preferred embodiment, it comprises:

a) contacting a filtered culture fluid with a dihydroxyboronyl bearing chromatographic support
b) eluting with a first eluting buffer and contacting this eluate directly with an anion exchange matrix bearing quaternary ammonium functional groups
c) eluting with a second eluting buffer and collecting the product therefrom.

22 Claims, No Drawings

PROCESS FOR THE PURIFICATION OF PROTEINS

This application is a continuation of application Ser. No. 08/475,260 filed Jun. 7, 1995.

The present invention is directed to a simple and efficient process for the recovery of a biologically active glycoprotein from a biological fluid in which it is contained.

The biologically active glycoprotein may be any of the known glycoproteins of biological and pharmaceutical interest.

More particularly, the process of the invention is suitable for recovering even highly glycosilated proteins, i.e. glycoproteins and glycopeptides having a sugar content higher than about 30% of their molecular weight.

A specific and preferred example of glycoprotein that can be conveniently purified according to the process of the invention is erythropoietin. The preparation of erythropoietin from various sources, including genetically engineered cells, is reported in several European patent applications or patents, such as EP-148605, EP-205564, EP-209539, EP-267678, and EP-649464.

As used herein, the term "erythropoietin" or "erythropoietin product" is intended to include naturally occurring erythropoietin, urinary derived human erythropoietin as well as non-naturally occurring polypeptides having an amino acid sequence and glycosylation sufficiently duplicative of that of naturally occurring erythropoietin to allow possession of in vivo biological properties causing bone marrow cells to increase production of reticulocytes and red blood cells and encompasses also "gene activated" erythropoietin such as that described in international patent application publication no.WO 93/09222, which was filed as PCT/US 92/09627, designating also the US, or WO 94/12650, claiming the priority of U.S. Ser. No. 07/985,586 that are herewith incorporated by reference.

The process of the invention is particularly suitable for the recovery of erythropoietin contained in a culture fluid of an erythropoietin producing cell culture.

When the specific activity of erythropoietin is referred to in this specification, it is intended to be determined according to an ELISA method (e.g. the one reported in this application: Human Erythropoietin ELISA method; R & D systems, Inc.), while the protein content of the samples is measured by the BCA Protein Assay. These analysis methods are reported in more details hereinbelow under the heading: "Analysis methods".

As used herein, the term "culture fluid" is preferably intended to refer to any fluid of artificial origin, such as the cell culture fluid of mammalian cells and in particular of genetically transformed mammalian cells.

Preferably, the "culture fluid" referred to in this application is a culture fluid that has been separated from cells and cell debris by filtration or ultrafiltration, as conventional in this art. Moreover, in the present disclosure, the term "filtered culture fluid" is used to indicate a culture fluid that has been separated from cells and cells debris by filtration or ultrafiltration, as conventional in this art.

"Producing cells" are preferably stabilized or non-stabilized cell lines of eukaryotic or preferably of mammalian origin that are capable, upon cultivation in a suitable medium, of producing the desired glycoprotein in a recoverable amount. Representative examples of these cells include fibroblasts, keratinocytes, epithelial cells (e.g., mammary epithelial cells, intestinal epithelial cells), endothelial cells, glial cells, neural cells, formed elements of the blood (e.g. lymphocytes, bone marrow cells), muscle cells and precursors of these somatic cell types. As mentioned, these cells are preferably of mammalian origin (e.g., mouse, rat, rabbit, cat, dog, pig, cow, bird, sheep, goat, horse, monkey, human) and most preferably they are from primates and humans. In particular, the term "producing cells" encompasses also transfected primary, secondary, and immortalized cells of vertebrate origin, particularly of mammalian origin, and most preferably of primate or human origin transfected with exogenous genetic material that directly or indirectly causes the cells to produce recoverable amounts of erythropoietin such as those described in international patent application publication no.WO 93/09222, which was filed as PCT/US 92/09627, designating also the US, or WO 94/12650, claiming the priority of U.S. Ser. No. 07/985,586, that are herewith incorporated by reference.

As mentioned, the process of the invention is suitable for recovering the desired glycoprotein from any such cultivation fluids and media.

The extensive application of genetic engineering technologies to the large scale preparation of biologically active protein has substantially enhanced the prospects of obtaining them in quantities than can satisfy their high demand. In several instances, however, their recovery from the production medium is troublesome, cumbersome and expensive. This is particularly the case when the protein is highly glycosilated, as mentioned above. Particularly in these instances, there continues to exist a need in the art for simple and efficient recovery procedures that are suitable for large scale production.

One object of the present invention is therefore a purification procedure which comprises:
a) contacting a filtered culture fluid, containing the biologically active glycoprotein to be isolated, with a dihydroxyboronyl bearing chromatographic matrix
b) eluting with a first elution buffer and contacting this eluate directly with an anion exchange matrix bearing quaternary ammonium functional groups
c) eluting the glycoprotein with a second elution buffer and collecting it.

As will be apparent from the complete reading of the present disclosure, these process steps allow a several-fold purification of a glycoprotein contained in a culture media, therefore they are effectively used as a first purification step in a multistep procedure that may include e.g. ion exchange, gel permeation or reverse phase chromatography.

According to the process of the invention a culture fluid containing the biologically active glycoprotein to be isolated is submitted to a procedure which comprises:
a) contacting a filtered culture fluid with a dihydroxyboronyl bearing chromatographic matrix
b) eluting with a first elution buffer and contacting this eluate directly with an anion exchange matrix bearing quaternary ammonium functional groups
c) eluting with a second elution buffer
d) ultrafiltering on a 5,000–30,000 D cutoff membrane,
e) optionally diafiltering to exchange the buffer to the one suitable for the next step, and
f) gel filtering on a separation resin having a separation range between 5,000 and 250,000 D.

Preferably the process of the invention comprises:
a) contacting a filtered culture fluid adjusted to pH 7.5–9.0 with a dihydroxyboronyl bearing chromatographic matrix equilibrated with a first equilibrating buffer which is an aqueous buffer at a concentration of 25–100 mM, with a ionic strength between 2 and 20 mS/cm$^2$ and a pH between 7.5 and 9.0,
b) washing subsequently with the first equilibrating buffer and then with the first equilibrating buffer containing from 10 to 100 mM of a 1,2-cys-diol containing low molecular weight substance, c) eluting with a first elution buffer which is an aqueous buffer having a pH between 7.5 and 11.0 containing a compound having 1-hydroxy, 2-amino groups at a concentration of 20–200 mM, possibly in the presence of a chaotropic agent at 2 to 8M, a cyanate acceptor at 2–40 mM, and a surfactant from 0.01% to 0.1% (w/w), d) contacting this eluate with an anion exchange matrix bearing quaternary ammonium functional groups equilibrated in a second equilibrating buffer which is an aqueous buffer having a pH between 7.5 and 11.0 and from 0.01% to 0.1% (w/w) of a surfactant, e) washing subsequently with the second equilibrating buffer and the same buffer containing additionally up to 50 mM salt, f) eluting with a second elution buffer having a pH between 7.5 and 11.0 in the presence of from 0.01% to 0.1% (w/w) of a surfactant and from 150 to 350 mM salt, g) ultrafiltering on a 5,000–30,000 D cutoff membrane, h) optionally diafiltering to exchange the buffer to one that is suitable for the next gel filtration step, and i) gel filtering on a separation resin having a separation range between 5,000 and 250,000 D.

"Dihydroxyboronyl bearing chromatographic matrices" refer to any known chromatographic matrix bearing a boronate function wherein the boron atom is stably bound to a carbon atom chain wherein the proximal carbon atom provides enough free electron density to remain bound to boron under the various conditions of use. Most preferably, this proximal carbon atom is an aromatic carbon atom, for example a carbon atom belonging to a possibly substituted benzene ring. Particularly preferred for use in the process of the invention are the so-called phenylboronate resins. Examples of these resins are reported in U.S. Pat. Nos. 4,562,251, 4,778,888 and 4,269,605, which are herein incorporated by reference. Among them, phenyl boronate agarose is currently the most preferred. This resin is at present commercially available, e.g. from Amicon Inc or Grace Inc., under the trade name MATREX GEL, including MATREX GEL PBA-10, PBA-30 and PBA-60. Currently, the most preferred phenyl boronate agarose is the one sold as MATREX GEL PBA-60, which is the one wherein m-aminophenyl boric acid is covalently coupled with agarose having a size range of 50–150 $\mu$m diameter spherical beads with a ratio 60–100 $\mu$M boronic acid/ml gel.

Currently, the most preferred use of these chromatographic matrices is in column chromatography systems, even if batchwise or other systems are not entirely ruled out.

When used in column chromatography systems, the dihydroxyboronyl bearing chromatographic matrix is preferably used at room temperature, preferably between 5 and 25° C., and most preferably between 10 and 20° C. with about 15° C. bearing the most preferred.

The above mentioned "first equilibrating buffer" is preferably selected from glycine, phosphate, trialkylammonium bicarbonate and 4-(2-hydroxyethyl)-1-piperazinoethane sulfonic acid (HEPES), at the indicated concentration range, ionic strength and pH. A particularly preferred concentration for this first equilibrating buffer is a concentration of about 50 mM, while a particularly preferred pH value is about 8.5, and a preferred conductivity of about 2.5 mS/cm$^2$.

The above mentioned "1,2-cys-diol containing low molecular weight substance" is any of the known low molecular weight compounds having 1,2-cys-diol functional groups, i.e. at least two hydroxy groups on adjacent carbon atoms are held or can assume a coplanar or quasi-coplanar configuration. Representative example of these compounds, that are in any case commonly known in the art, are small open-chain polyols such as sorbitol, mannitol, adonitol, arabitol, glycerol, erythritol, and cis-inositol, and closed-chain monosaccharides such as ribose and mannose, with sorbitol being currently the most preferred. Particularly preferred is the use of 1,2-cys-diol containing low molecular weight substance at a concentration of about 50 mM.

The above mentioned "compound having 1-hydroxy, 2-amino groups" which is the main constituent of said "first elution buffer" is any compound having such functional groups and capable of forming an aqueous buffer in the pH range indicated above. Representative example of any such compounds are: 2-amino-2-hydroxymethyl-1,3-propanediol, which is known also as TRIS or tris (hydroxymethyl)aminoethane; bis(hydroxymethyl) aminoethane; N-[2-hydroxy-1,1-bis(hydroxymethylethyl] glycine, which is known also as tricine; and N,N-bis(2-hydroxyethyl)glycine, which is known also as bicine. They are preferably employed at a concentration of about 20–100 mM, with about 50 mM being currently most preferred. Preferably, the first elution buffer is adjusted at a pH of about 8.5.

Preferably, the "second equilibrating buffer" and the "second elution buffer" have the above defined compound having 1-hydroxy, 2-amino groups as their main component. In this case, its preferred concentration is between 20 and 200 mM.

A "chaotropic agent" is an agent favoring the salting-in of a proteinaceus material, and thus its solubilization in an aqueous medium, generally because of its dissociating properties.

Representative examples of chaotropic agents are urea and its derivatives and guanidine. The chaotropic agent, if present, is employed in a concentration between 2 and 8M, with about 4–6M being preferred.

A cyanate acceptor is any of the known substances capable of readily binding CNO$^-$ ions that may form as a result of the hydrolysis of urea.

Glycine is preferred as a cyanate acceptor. For its use in the process of the invention, glycine is preferably employed at a concentration from 2 to 40 mM and most preferably at about 20 mM.

As mentioned above, the "surfactant", is any of the known substances that reduce the surface tension, i.e. the force that acts at the surface of liquids to reduce their surface area, can be usefully employed in the process of the invention. Preferred examples of surfactants are the polyoxyethylene sorbitan derivatives of fatty acids known as "Tween", with "Tween 20" (i.e. polyoxyethylene sorbitan monolaurate) being currently preferred. Currently, the surfactant, if present, is preferably employed at a concentration of about 0.01–0.1% (w/w), with about 0.01% being currently most preferred.

The above mentioned anion exchange matrix bearing quaternary ammonium functional groups is any of the known and commercially available anion exchange matrices having said functional groups. Preferred for use in the process of the invention are agarose or cellulose based matrices, such as microcrystalline cellulose or crosslinked agarose. Also particularly preferred are those matrices bearing diethyl aminoethyl, triethyl aminomethyl or trimethyl aminomethyl functional groups.

A particularly preferred anion exchange matrix is trimethyl aminomethyl crosslinked agarose, which is commercially available e.g. as Q-Sepharose (Pharmacia AB). The chromatographic step involving these matrices is most preferably conducted as a column chromatography which is conducted at room temperature.

When a salt is added to a washing or elution buffer as reported above, it is added to increase the ionic strength of the buffer, as conventional in the art. Any of the salts conventionally used in the art can be employed in the process of the invention for this purpose, with NaCl being one of those most frequently and conveniently used.

The ultrafiltration step is conducted as conventional in the art, using a tangential flow system or a stirred cell system. Preferably, the membrane is a polysulfonic membrane or regenerated cellulose membrane of the types commercially available e.g. from Millipore Inc. or Amicon Inc. Currently preferred for use in the process of the invention are those membranes having a cutoff of 10,000.

The ultrafiltrate is then optionally submitted to diafiltration according to procedures known per se in the art, preferably in the same buffer that is being used for the next gel filtration step. This gel filtration buffer is an aqueous buffer having a pH between 6 and 8. The salt is present preferably from 100 to 200 mM in this buffer and still more preferably, the salt is 100 mM and the pH is about 7.4–7.5.

The conventional gel filtration matrices can be conveniently used in this process step. Representative examples of these matrices are polydextranes crosslinked with acrylamides, such as high mechanical strength composite hydrophilic gels prepared by covalently crosslinking allyl dextran with N,N'-methylene bisacrylamide and crosslinked cellulose gels. Commercially available crosslinked dextrane-acrylamides are known under the trade name SEPHACRYL and are available from Pharmacia AB. A preferred SEPHACRYL gel is SEPHACRYL S-200 HR, which has a bead size of 25–75 $\mu$m and its crosslinking is controlled so that it has a fractionation range for globular protein of 5,000–250,000 D.

Examples of crosslinked cellulose gels are those commercially available crosslinked porous cellulose gels, e.g. GLC 300 (average particle size 44–125 $\mu$m) or GLC 1,000 (average particle size 53–125 $\mu$m) that are available from Amicon Inc.

The process of the invention is particularly apt to large scale production, since it consists of a sequence of steps that are easily scalable without the major drawbacks of the known ones.

Moreover, it employees only aqueous solvents, and this represents a further advantage, as it is appreciated by those skilled in the art.

Additionally, it allows passing from its first chromatographic step (i.e. the one with the dihydroboronyl matrix) to its second chromatographic step (i.e. the one with the anion exchange matrix) by directly transferring the eluate from the first step to the second one, without requiring any solvent exchange or adjustment.

In addition to making the overall opearations easier, this feature of the process of the invention contributes to improving the recovery yields.

The process of the invention in fact allows the recovery of an erythropoietin product having an average specific activity of 145,000–175,000 IU/mg, starting from a filtered cell fluid with an average specific activity of 500–2,000 IU/mg.

Moreover, the combined first and second chromatographic step allow a 60–100 fold purification of the initial culture fluid, with an overall purification factor of 110–150 fold for the complete process.

As in the case of erythropoietin, the glycoprotein product recovered at the end of the process of the invention may be isolated as a solid after salt removal and lyophilization as conventional in the art, or the obtained solution can be solvent exchanged, e.g. by diafiltration, to have a solution suitable for pharmaceutical formulation, such as one of those described in EP 430200, which is herein incorporated by reference.

The following example is illustrative only and is not to be construed to limit the scope of the claimed invention.

EXAMPLE

The supernatant of a culture of a human erythropoietin producing cell obtained as described in example 21 of WO 93/09222 containing approximately 20 mg of erythropoietin is filtered on a mixed membrane cartridge (1.2 and 0.5 $\mu$m; Opticap, Millipore Inc) and then ultrafiltered on a 30,000 D regenerated cellulose spiral cartridge SIY30 (Amicon Inc) and diafiltered with water and 0.05M HEPES pH 8.5, conductivity 2.5 mS/cm$^2$. The ultrafiltrate is loaded on a phenylboronate agarose chromatographic column (120 ml swollen resin; PBA 60, Amicon Inc) equilibrated with 0.05M HEPES pH 8.5 containing 0.01% Tween 20 (Buffer A) and kept at about 10–15° C. by water refrigeration. The flow rate is set at about 2–4 column volumes (CV)/h. After having washed with Buffer A until the baseline stabilizes [optical density (OD) at 280 nm], washing is continued with 0.05M HEPES pH 8.5 containing 0.01% Tween 20 and 0.05M sorbitol (Buffer B). Elution is carried out with 0.02M TRIS pH 8.5 containing 6M urea, 0.02M glycine and 0.01% Tween 20 (Buffer C) and the peak (OD at 280 nm) that elutes is collected (about 4–5 CV; yield 70–80%, purification factor about 20-fold) and directly loaded onto a trimethyl aminomethyl crosslinked agarose anion exchange resin (25 ml swollen resin; Q-Sepharose FF, Pharmacia AB) equilibrated with 0.02M TRIS pH 8.5 containing 0.01% Tween 20 (Buffer D). After washing, at a constant flow rate, with Buffer D until baseline stabilizes, and then with Buffer D containing also 0.05 M NaCl (Buffer E), elution is done with 0.02M TRIS pH 8.5 containing 0.01% Tween 20 and 0.15 M NaCl (Buffer F). The peak (OD 280 nm) is collected (recovery about 80%) and concentrated by ultrafiltration with a stirred cell having a membrane of 10,000 D cutoff (YM10, Amicon).

The concentrated solution is loaded on a crosslinked dextrane-acrylamide gel filtration column (Sephacryl S 200; Pharmacia AB) equilibrated with 0.02M TRIS pH 7.4 containing 0.15 M NaCl (Buffer G) and eluted with the same buffer. Fractions are collected and those containing the erythropoietin product (ELISA assay) are pooled and concentrated by ultrafiltration as described above.

Analysis Methods

ELISA:

The specific activity of the erythropoietin product obtained according to the process described above is measured by the Human EPO ELISA method that is known from and commercially available as QUANTIKINE IVD (R&D SYSTEMS Inc).

Protein assay:

Protein assay is conducted by the BCA Protein Assay Reagent method (Pierce Chemical Co) that is a method that combines the biuret reaction (protein reduction of $Cu^{2+}$ to $Cu^{1+}$ in an alkaline medium) with the highly specific reaction of bicinchoninic acid (BCA) for $Cu^{1+}$.

HPLC analysis:

Instrument: Waters 616 LC System equipped with a PDA detector model 996

Column: Vydac protein $C_4$, 3 $\mu$m, 4.6×250 mm

Mobile phase: A) 0.1% aqueous trifluoroacetic acid:acetonitrile, 95:5, B) 0.1% aqueous trifluoroacetic acid:acetonitrile, 5:95

Gradient: min (% B): 5 (5), 50 (95)
Flow rate: 1 ml/min
SDS-PAGE analysis:

SDS-PAGE analysis is done on a Phast System, Pharmacia AB and the densitometry measurements are done with a Flying Spot scanning densitometer CS-9301 PC, Shimadzu Co), according to the manufacturer's instructions and common knowledge in this field.

Analytical Data and Results

Having collected data from several runs, the specific activity of the erythropoietin product of the cell supernatant resulted in the range 500–2,000 IU/mg; the specific activity of the erythropoietin product recovered after the first chromatographic step is about 35,000–95,000 IU/mg; the specific activity of the erythropoietin product recovered at the end of the procedure described in the above example is, in the average, about 145,000–175,000 IU/mg.

The HPLC analysis as well as the SDS-PAGE analysis conducted according to the methods reported above showed that the the erythropoietin product recovered at the end of the procedure had a principal peak which represented more than 92% of the area under the curve (AUC).

We claim:

1. A process for the purification of biologically active erythropoietin which comprises:
    a) contacting a filtered culture fluid, containing the biologically active glycoprotein to be isolated, with a dihydroxyboronyl bearing chromatographic matrix
    b) eluting with a first elution buffer and contacting this eluate directly with an anion exchange matrix bearing quaternary ammonium functional groups
    c) eluting the erythropoietin with a second elution buffer and collecting it.

2. A process for the purification of biologically active erythropoietin which comprises:
    a) contacting a filtered culture fluid, containing the erythropoietin to be isolated, with a dihydroxyboronyl bearing chromatographic support
    b) eluting with a first eluting buffer
    c) contacting this eluate directly with an anion exchange matrix bearing quaternary ammonium functional groups
    d) eluting with a second eluting buffer
    e) ultrafiltering on a 5,000–25,000 D cutoff membrane,
    f) gel filtering on a separation resin having a separation range between 5,000 and 250,000 D.

3. A process for the purification of biologically active erythropoietin which comprises:
    a) contacting a filtered culture fluid adjusted to pH 7.5–9.0 with a dihydroxyboronyl bearing chromatographic support equilibrated with a first equilibrating buffer which is an aqueous buffer at a concentration of 25–100 mM, with a ionic strength between 2 and 20 mS/cm$^2$ and a pH between 7.5 and 9.0,
    b) washing subsequently with the first equilibrating buffer and then with the first equilibrating buffer containing from 10 to 100 mM of a 1,2-cys-diol containing low molecular weight substance,
    c) eluting with a first eluting buffer which is an aqueous buffer having a pH between 7.5 and 11.0 containing a compound having 1-hydroxy, 2-amino groups at a concentration of 20–200 mM,
    d) contacting this eluate with an anion exchange matrix bearing quaternary ammonium functional groups equilibrated in a second equilibrating buffer which is an aqueous buffer having a pH between 7.5 and 11.0 and from 0.01% to 0.1% (w/w) of a surfactant,
    e) washing subsequently with the second equilibrating buffer and the same buffer containing additionally up to 50 mM salt,
    f) eluting with a second eluting buffer having a pH between 7.5 and 11.0 in the presence of from 0.01% to 0.1% (w/w) of a surfactant and from 150 to 350 mM salt,
    g) ultrafiltering on a 5,000–30,000 D cutoff membrane, and
    h) gel filtering on a separation resin having a separation range between 5,000 and 250,000 D.

4. The process of claim 2, wherein the ultrafiltration obtained in step (e) is diafiltered to exchange the buffer to the one suitable for performing step (f).

5. The process of claim 3, wherein step (c) is performed in the presence of a choatropic agent at 2 to 8M, a cyanate acceptor at 2–40M, and a surfactant from 0.02% to 0.1% (w/w).

6. The process of claim 3, wherein the ultrafiltration obtained in step (g) is diafiltered to exchange the buffer to the one suitable for performing the gel filtration step (h).

7. A process according to any one of claims 1, 2, or 3 wherein the dihydroxyboronyl bearing chromatographic support is a phenylboronate agarose.

8. A process according to any one of claims 1, 2, or 3 wherein the first equilibrating buffer is selected from the group consisting of glycine, phosphate, trialkylammonium bicarbonate and 4-(2-hydroxyethyl)-1-piperazinoethane sulfonic acid.

9. A process according to claim 3 wherein the first equilibrating buffer is 4-(2-hydroxyethyl)-1-piperazinoethane sulfonic acid at a concentration of about 0.05 M.

10. A process according to claim 9 wherein the pH of the first equilibrating buffer is about 8.5.

11. A process according to claim 3 wherein the 1,2-cys-diol containing low molecular weight substance is a small open-chain polyol selected from the group consisting of sorbitol, mannitol, adonitol, arabitol, glycerol, erythritol, and cis-inositol, and a closed-chain monosaccharide selected from the group consisting of ribose and mannose.

12. A process according to claim 11 wherein the 1,2-cys-diol containing low molecular weight substance is sorbitol.

13. A process according to claim 11 or 12 wherein the 1,2-cys-diol containing low molecular weight substance is present in a concentration of about 0.05 M.

14. A process according to claim 3 wherein the second equilibrating buffer contains a compound having 1-hydroxy, 2-amino groups at a concentration of 0.02–0.2 M.

15. A process according to claim 3 wherein the second eluting buffer contains a compound having 1-hydroxy, 2-amino groups at a concentration of 0.05 M.

16. A process according to claim 3 wherein the compound having 1-hydroxy, 2-amino groups is selected from the group consisting of 2-amino-2-hydroxymethyl-1,3-propanediol, bis(hydroxymethyl)aminoethane, N-[2-hydroxy-1,1-bix(hydroxymethylethyl)]glycine, and N,N-bis(2-hydroxyethyl)glycine.

17. A process according to claim 6 wherein the chaotropic agent is selected from urea and its derivatives, and guanidine.

18. A process according to claim 17 wherein the chaotropic agent is 6M urea.

19. A process according to claim 6 wherein the cyanate acceptor is glycine.

20. A process according to claims 1, 2, or 3 wherein the anion exchange matrix bearing quaternary ammonium functional groups is selected from the group consisting of a microcrystalline cellulose matrix, a crosslinked agarose matrix, a microcrystalline cellulose matrix bearing diethyl aminoethyl, triethyl aminomethyl or trimethyl aminomethyl functional groups, and a crosslinked agarose matrix bearing diethyl aminoethyl, triethyl aminomethyl or trimethyl aminomethyl functional groups.

21. A process according to claim 3 wherein the anion exchange matrix is trimethyl aminomethyl agarose.

22. A process according to claims 2 or 3 wherein the gel filtration is carried out with controlled pore crosslinked dextrane-acrylamide gel matrix.

* * * * *

UNITED STATES PATENT AND TRADEMARK OFFICE
CERTIFICATE OF CORRECTION

PATENT NO. : 5,981,716
DATED : November 9, 1999
INVENTOR(S) : Zanette et al.

It is certified that error appears in the above-identified patent and that said Letters Patent is hereby corrected as shown below:

In [56] under 'OTHER PUBLICATIONS', the File Caplus entry, second line, delete the term "Fro" and insert therefor the word --For--.
In Column 2, line 21, delete the word "than" and insert therefor the word --that--.
In Column 3, lines 1, 63 and 65, delete ther term "cys" and insert therefor the term --cis--.
In Column 3, line 44, delete the word "boric" and insert therefor the word --boronic--
In Column 4, line 7, delete ther term "cys" and insert therefor the term --cis--.
In Claim 1, Column 7, line 28, delete the term "glycoprotein" and insert therefor --erythropoietin--.
In Claim 3, Column 7, line 60, delete the term "cys" and insert therefor the term --cis--.
In Claim 11, Column 8, line 44, delete the term "cys" and insert therefor the term --cis--.
In Claim 12, Column 8, line 50, delete the term "cys" and insert therefor the term --cis--.
In Claim 13, Column 8, line 53, delete the term "cys" and insert therefor the term --cis--.
In Claim 16, Column 8, line 66, delete the term "bix" and insert therefor the term --bis--.
In claim 17, column 9, line 1, delete the numeral "6" and insert therefor --3--.
In claim 19, column 9, line 6, delete the numeral "6" and insert therefor --3--.

Signed and Sealed this

Fifth Day of December, 2000

*Attest:*

*Attesting Officer*

Q. TODD DICKINSON
*Director of Patents and Trademarks*